United States Patent
Bansal

(10) Patent No.: US 10,682,382 B2
(45) Date of Patent: Jun. 16, 2020

(54) COMPOSITION FOR RELIEVING PAIN, STRESS AND INSOMNIA

(71) Applicant: Ashvany Kumar Bansal, Maharashtra (IN)

(72) Inventor: Ashvany Kumar Bansal, Maharashtra (IN)

( * ) Notice: Subject to any disclaimer, the term of this patent is extended or adjusted under 35 U.S.C. 154(b) by 753 days.

(21) Appl. No.: 15/115,527

(22) PCT Filed: Feb. 4, 2015

(86) PCT No.: PCT/IN2015/000067
§ 371 (c)(1),
(2) Date: Jul. 29, 2016

(87) PCT Pub. No.: WO2015/132800
PCT Pub. Date: Sep. 11, 2015

(65) Prior Publication Data
US 2017/0007655 A1    Jan. 12, 2017

(30) Foreign Application Priority Data

Feb. 4, 2014   (IN) ........................... 394/MUM/2014

(51) Int. Cl.
| | | |
|---|---|---|
| *A61K 36/31* | (2006.01) | |
| *A61K 36/54* | (2006.01) | |
| *A61K 35/644* | (2015.01) | |
| *A61K 36/185* | (2006.01) | |
| *A61K 9/00* | (2006.01) | |
| *A61K 31/122* | (2006.01) | |

(52) U.S. Cl.
CPC ............ *A61K 36/31* (2013.01); *A61K 9/0014* (2013.01); *A61K 31/122* (2013.01); *A61K 35/644* (2013.01); *A61K 36/185* (2013.01)

(58) Field of Classification Search
CPC ................................. A61K 36/31; A61K 36/54
USPC ........................................ 424/755, 739, 420
See application file for complete search history.

(56) References Cited

U.S. PATENT DOCUMENTS

2013/0072575 A1   3/2013   Chin et al.

FOREIGN PATENT DOCUMENTS

| CN | 101085300 A | | 12/2007 |
|---|---|---|---|
| CN | 101480474 A | * | 7/2009 |
| CN | 101480474 A | | 7/2009 |
| CN | 101816470 A | | 9/2010 |
| CN | 101843878 A | | 9/2010 |
| JP | 2012/246324 A | | 12/2012 |
| JP | 2012246324 A | * | 12/2012 |

OTHER PUBLICATIONS

Firenzuoli et al., "Herbal Medicine Today: Clinical and Research Issues", eCAM 2007; 4(S1) 37-40 (Year: 2007).*

* cited by examiner

*Primary Examiner* — Michael Barker
*Assistant Examiner* — Deborah A Davis
(74) *Attorney, Agent, or Firm* — Saliwanchik, Lloyd & Eisenschenk

(57) ABSTRACT

The present invention relates to a composition for relieving one or more of the conditions of pain, stress and insomnia comprising *Brassica compestris*, Bees wax and *Dryobalanops camphora*. The present invention also provides a formulation comprising the composition of the present invention as well as method for preparation thereof, uses thereof and method of treatment of one or more of the conditions of pain, stress and insomnia.

18 Claims, 4 Drawing Sheets

COMPOSITION FOR RELIEVING PAIN, STRESS AND INSOMNIA

CROSS REFERENCE TO A RELATED APPLICATION

This application is a National Stage Application of International Application Number PCT/IN2015/000067, filed Feb. 4, 2015; which claims priority to India Patent Application No. 394/MUM/2014, filed Feb. 4, 2014; which are incorporated herein by reference in their entirety.

FIELD OF INVENTION

The invention relates to a composition for relieving at least one of the conditions of pain, stress and insomnia, a process for preparing the same, uses thereof and method of treatment thereof.

BACKGROUND OF THE INVENTION

There are various drugs and formulations available for treating pain, stress and sleep disorders. Pain is a major symptom in many medical conditions and can significantly interfere with a person's quality of life and general functioning. Pain ranges from mild discomfort or dull distress to acute often unbearable agony and may be generalized or localized. NSAIDs (Non-Steroidal Anti-inflammatory Drugs) such as aspirin, ibuprofen and naproxen, are among the most frequently used prescription and over-the-counter drugs used to alleviate symptoms in acute and chronic inflammatory conditions inducing pain. But patients continue to face the significant challenge of their serious complications like gastrointestinal (GI) and renal adverse effects.

Stress is increasing tremendously, particularly among the urban population resulting in various types of stress related disorders. Numerous treatments are used to overcome stress ranging from aromatherapy to administration of therapeutic drugs. Aroma therapy involves inhalation of essential oils. However, it is observed that inhalation may or may not be suitable to all as it can cause irritation to sensitive mucous membranes and damage the smell receptors inside nose. Prolonged inhalation of concentrated essential oils can cause headaches, vertigo, dizziness, nausea, and lethargy. Thus, such therapy for relieving stress could rather aggravate stress or cause other undesirable effects. Administration of therapeutic drugs by oral or intravenous route needs supervision and intervention of a doctor, posing limitations to their application. Further they have delayed onset of action and adverse side effects for e.g. Benzodiazepines, which may be used to treat stress have potentially addictive effects on the patient.

Insomnia, or sleeplessness, a sleep disorder caused by stress or of other etiology is highly prevalent and affects approximately 30% of the general population. Chronically restricted sleep has today become a widespread and serious problem in our society. Insomnia impairs cognitive and physical functioning and is associated with a wide range of impaired daytime functions across a number of emotional, social, and physical domains and could lead to other disorders and health risks. At present the frontline therapy for insomnia are antihistamines, benzodiazepines and non-benzodiazepines. These drugs have various harmful effects for instance drugs for insomnia are habit forming and are thus harmful to the patient. Newer sleep-inducing drugs include Zolpidem, which again show many side-effects the most important being next-day drowsiness, rebound insomnia, dependency and abuse.

Further, persistent use of drugs leads to patients developing resistance for such drugs and decreases its response to further treatment.

Topical formulations available for the treatment of pain; stress and insomnia are also not devoid of any adverse side effects. For example, salicylate and capsaicin based topical formulations for the treatment of pain are irritants to the skin and both of which are preferably avoided even in trace amounts. Topical preparation of St. John's wort for the treatment of stress may increases skin sensitivity to sunlight and cause rashes. Topical formulations to treat insomnia are not very common and the few tried are generally not found to be very effective.

Thus, the topical formulations available are not very effective for relieving pain, stress or insomnia. On the contrary, the available topical formulations either have side-effects or are not capable of effectively relieving an individual of pain, stress and insomnia.

Therefore, there is a need for a safer composition which can be formulated for topical delivery and can relieve one or more of the conditions selected from pain, stress and insomnia.

SUMMARY OF THE INVENTION

Accordingly, in one aspect the present invention provides a composition for relieving one or more of the conditions of pain, stress and insomnia.

In one embodiment, the present invention provides a composition comprising *Brassica compestris*, Bees wax and *Dryobalanops camphora*.

In one embodiment, the composition of the present invention comprises *Brassica compestris* oil, Bees wax and *Dryobalanops camphora* oil.

In some embodiments, the present invention provides a composition comprising *Brassica compestris* oil, Bees wax and *Dryobalanops camphora* for relieving at least one or more or all the conditions of pain, stress and insomnia.

In some embodiments, the present invention provides a composition comprising 40 to 75 weight parts of *Brassica compestris* oil, 15 to 50 weight parts of Bees wax and 1 to 20 weight parts of *Dryobalanops camphora*.

In another aspect the present invention provides a method for preparing composition for relieving one or more of the conditions of pain, stress and insomnia.

In one embodiment, the present invention provides a method for preparing a formulation for relieving at least one of the conditions of pain, stress and insomnia comprising: heating 40 to 75 weight parts of *Brassica compestris* oil at a temperature of 60° C.-225° C. for a specific time period; mixing 15 to 50 weight parts of Bees wax in the hot *Brassica compestris* oil at least until the bees wax is dissolved and mixing 1 to 20 weight parts of *Dryobalanops camphora* in the mixture of *Brassica compestris* oil and Bees wax.

In one embodiment the present invention provides a method for preparing a formulation for relieving at least one of the conditions of pain, stress and insomnia comprising: heating 40 to 75 weight parts of *Brassica compestris* oil at a temperature of 60° C.-225° C. for a specific time period; mixing 15 to 50 weight parts of Bees wax in the hot *Brassica compestris* oil at least until the bees wax is dissolved; taking the mixture away from the heat and mixing 1 to 20 weight parts of *Dryobalanops camphora*.

In one embodiment, the time period for heating of *Brassica compestris* oil is a time period sufficient to attain the temperature of 60° C.-225° C.

In one embodiment, the heating of *Brassica compestris* oil is carried out at a temperature of 60° C.-100° C. In such embodiment, the time period for heating of *Brassica compestris* oil is a time period sufficient to attain the temperature of 60° C.-100° C.

In an embodiment, the present invention provides use of the composition comprising *Brassica compestris* oil, Bees wax and *Dryobalanops camphora* oil for relieving at least one or more or all the conditions of pain, stress and insomnia.

In one embodiment, the present invention provides the method of treatment of at least one of the conditions of pain, stress and insomnia comprising of applying the composition of the present invention at affected areas, inflamed areas, head or all over the body.

BRIEF DESCRIPTION OF THE DRAWINGS

Other objects, features, and advantages of the invention will be apparent from the following description when read with reference to the accompanying drawings.

DESCRIPTION OF THE INVENTION

Figure 1:
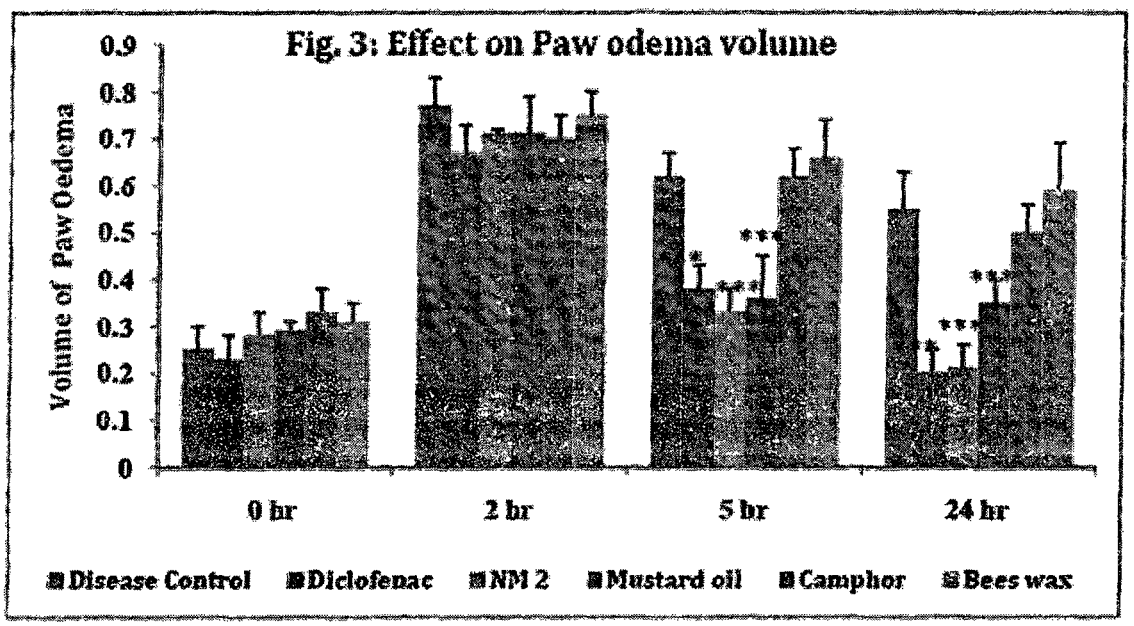
FIG. 1 illustrates effect on carrageenan induced paw odema in rats by NM-2 (the formulation of the present invention) in comparison with its individual ingredients that is mustered oil, camphor and bees wax and commercially available preparation Dicolfenac.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The present invention discloses a composition which can relieve at least one of the conditions of pain, stress and insomnia.

In an embodiment, the present invention provides a composition comprising *Brassica compestris*, Bees wax and *Dryobalanops camphora*.

*Dryobalanops camphora* may be included in the composition of the present invention either in the crystal form or oil form. *Dryobalanops camphora* oil and *Dryobalanops camphora* in crystal form may be used interchangeably in the composition of the present invention.

In one embodiment, the composition of the present invention comprises *Brassica compestris* oil, Bees wax and *Dryobalanops camphora* oil.

In some of the embodiments, the present invention provides a composition comprising *Brassica compestris* oil, Bees wax and *Dryobalanops camphora* for relieving at least one or more or all the conditions of pain, stress and insomnia.

The active ingredients of the composition can be combined in any number of ways to optimize the desired effects. According to some of the embodiments, the composition of the present invention comprises 40 to 75 weight parts of *Brassica compestris* oil, 15 to 50 weight parts of Bees wax and 1 to 20 weight parts of *Dryobalanops camphora*.

According to still further embodiments, the composition of the present invention comprises 55 to 65 weight parts of *Brassica compestris* oil, 25 to 35 weight parts of Bees wax and 3 to 13 weight parts of *Dryobalanops camphora*.

In one of the embodiment the ratio of *Brassica compestris* oil, Bees wax and *Dryobalanops camphora* is approximately about 1:0.5:0.1.

However, as may be recognized by those skilled in the art based on the teachings herein, the exact composition can be varied and relative proportions of the active ingredients can be varied in any manner to provide increases or decreases in particular effects.

The composition of the above embodiments may optionally include one or more other ingredients to provide additional relief or other benefits. For example the composition may further comprise of one or more of other active ingredient(s) like natural active ingredients for e.g. extracts, tincture, essential oil, infused oil or any other oil. Preferably, such natural active ingredients are selected from clove oil, ginger extract or oil, sesame oil, castor oil, guggul, natural perfumes or combinations thereof. The other active ingredient(s) may be synthetic active ingredients. Such natural or synthetic active agent that may be included in the composition of the present invention may be selected from but not limiting to a group consisting of a circulation increasing agent, a joint or muscle soothing agent and a muscle membrane stabilizer.

In additional embodiments, the composition may optionally include one or more of pharmaceutically acceptable excipients. Examples of such optional pharmaceutically acceptable excipients include carriers; base components for example water, propylene glycol, glycerol, polyethylene glycols, silicones, and/or an oil such as vegetable oil, peanut oil, castor oil, and cocoa butter and liquid paraffin; surfactants; thickening agents for example aluminum stearate and hydrogen lanolin; gelling agents; stabilizing agents; emulsifying agents; dispersing agents; suspending agents; humectants; emollients; cooling component, a circulation increasing component, acidic or alkaline substances; buffering agents; anti-crystalline agents; lubricating agents; coloring agents; perfumes or fragrance; foaming agents; diluents; fillers; binding agents or preservatives.

In a still further embodiment, the invention provides a formulation comprising of composition of the above embodiments. In some of the embodiments, the formulation may comprise of the acceptable excipients so as to formulate the composition into a topical formulation selected from one or more of the group consisting of a water-based formulation, a silicone-based formulation, a petroleum-based formulation and a natural oil-based formulation. In preferred embodiments, the formulation includes excipients for natural oil-based formulation.

According to another embodiment, further additives may be added to the formulation to enhance the stability, texture, colour, odor and other properties.

In some of the embodiments, formulations comprising composition of the above embodiments may be formulated in the form of an oil, gel, cream, lotion, balm or spray.

In another aspect the present invention provides a method for preparing composition for relieving one or more of the conditions of pain, stress and insomnia.

In one embodiment, the present invention provides a method for preparing a formulation for relieving at least one of the conditions of pain; stress and insomnia comprising: heating 40 to 75 weight parts of *Brassica compestris* oil at a temperature of 60° C.-225° C. a specific time period; mixing 15 to 50 weight parts of Bees wax in the hot *Brassica compestris* oil at least until the bees wax is dissolved and mixing 1 to 20 weight parts of *Dryobalanops camphora*.

In one embodiment the present invention provides a method for preparing a formulation for relieving at least one of the conditions of pain, stress and insomnia comprising: heating 40 to 75 weight parts of *Brassica compestris* oil at a temperature of 60° C.-225° C. for a specific time period; mixing 15 to 50 weight parts of Bees wax in the hot *Brassica compestris* at least until the bees wax is dissolved; taking the mixture away from heat, and mixing 1 to 20 weight parts of *Dryobalanops camphora*.

In one embodiment, heating of *Brassica compestris* oil at temperature of 60° C.-225° C. is carried out for the time period of about one minute to about fifteen minutes. Such time period may be varied depending upon the quantities and scale at which the formulation is made so as to achieve the temperature of 60° C.-225° C.

In one embodiment, the heating of *Brassica compestris* oil is carried out at a temperature of 60° C.-100° C. In such embodiment, the time period for heating of *Brassica compestris* oil is a time period sufficient to attain the temperature of 60° C.-100° C.

In one embodiment the *Brassica compestris* oil is 55 to 65 weight parts of the formulation.

In one embodiment the Bees wax is 25 to 35 weight parts of the formulation.

In one embodiment the *Dryobalanops camphora* in crystal form or *Dryobalanops camphora* oil is 3 to 13 weight parts of the formulation.

According to another embodiment, the process further involves addition of preservatives, emulsifiers, other additives and pharmaceutically acceptable agents and/or excipients.

In an embodiment, the present invention provides use of the composition comprising *Brassica compestris* oil, Bees wax and *Dryobalanops camphora* for relieving at least one or more or all the conditions of pain, stress and insomnia.

In an embodiment, the present invention provides a method of treatment of at least one of the conditions of pain, stress and insomnia comprising of applying the composition of the present invention in a quantity sufficient to cover affected areas, inflamed areas, head or all over body as per the need of the subject. The composition would be administered to a subject as needed, as desired, or as advised by a medical practitioner, pharmacist, attendant physician, medical herbalist, naturopath, or veterinarian.

As will be appreciated, the dose administered, the period of administration, and the general administration regime may differ between subjects depending on variables such as the severity of the symptoms, and the age and/or general health of the subject. In general, when the composition is converted into a formulation suitable for topical administration, the administration regime for topical treatment is application to the affected areas 1 time or 2 times or 3-4 times or more than 4 times in a day for a day or a number of days depending on the severity of pain, stress or insomnia.

In one embodiment in case of subject with pain a gentle massage of formulation on and near affected area for about 2 minutes to 10 minutes or till the time the warmness in affected area is felt.

In one embodiment to relieve stress gentle massage of formulation on forehead for 10 seconds to 1 minute or/and massage on the leg below knee and especially sole for about 5 minutes to 20 minutes is carried out.

In one embodiment in case of subject with insomnia, a gentle massage of formulation on the leg below knee and specially sole for about 5 minutes to 20 minutes is carried out, the same is found to induce sleep in the subject.

In some embodiments, the formulation or composition is applied before going to bed.

The formulation or composition relaxes the body and the mind from the stress and helps to get sound sleep. The formulation or composition has been found effective in relieving pain and inflammation. The composition or formulation of the present invention can be used for curing the inflamed areas reducing the pain and swelling associated with muscle pull, sprains, arthritis, rheumatoid arthritis, bursitis, neuralgia, myositis, carpel tunnel syndrome, internal injuries, and other conditions inflicting pain. It is also useful during strain of muscles during sports, any other activity or accident.

According to another embodiment, the composition is applied before performing a strenuous physical activity such as a marathon, racing, long walks or driving, strenuous work or any other strenuous activities which may cause pain or stress or resulting sleeplessness. Thus, the composition may be used for preventing pain, stress and insomnia related to pain or stress or insomnia as such.

The composition of the present invention is effective in relieving pain, stress and insomnia and comprises of very few components that is to say in one embodiment the composition of the present invention contains only three ingredients. Also, the method for preparing the formulation does not require complicated steps, equipments, machineries, set-up or very high energies. Hence, the composition and process of the present invention are very advantageous for the reasons that they are very simple, economic and effective for the treatment of more than one condition of pain, stress and insomnia.

Reference will now be made in detail to certain embodiments of the invention. While the invention will be described in conjunction with the enumerated examples, it will be understood that they are merely to illustrate the invention and not intended to limit the invention to those embodiments. On the contrary, the invention is intended to cover all alternatives, modifications, and equivalents, which may be included within the scope of the present invention as defined by the claims. Since modifications of the disclosed embodiments, many methods and materials similar or equivalent to those described herein, which could be used in the practice of the present invention incorporating the spirit and substance of the invention may occur to person skilled in the art, the invention should be construed to include everything within the scope of the disclosure. One skilled in the art will recognize, the present invention is in no way limited to the methods and materials described.

EXAMPLES

Example 1

Preparation of Topical Oil Formulation

A topical oil formulation as an exemplary embodiment was prepared as follows.

Brassica compestris oil 62.50 ml was heated to a temperature of 100° C., for about 3 to 10 minutes. Bees wax 31.25 gm was mixed into the hot Brassica compestris oil so as to completely dissolve the Bees wax. The mixture was taken away from heat and Dryobalanops camphora 6.25 gm was added and mixed. The mixture was allowed to cool to room temperature. It was then bottled.

Example 2

Evaluation of Anti-Inflammatory and Analgesic Effect of the Topical Oil Formulation in Comparison with its Individual Ingredients The aim of the study was to evaluate the topical oil formulation prepared as per Example 1 (herein referred to as NM-2) and its individual ingredients for relieving pain and associated inflammation.

Materials and Methods:

Carragenen induced paw oedema was used to test the acute anti-inflammatory and analgesic properties of the NM-2 and its individual ingredients.

Rationale:

This model tests the ability of drugs to inhibit the oedema produced in the hind paw of the rat after injection of a phlogistic agent (irritant) such as carrageenan. The volume of the injected paw is measured before and after application of the irritant and the paw volume of the treated animals is compared with that of the disease control group.

Procedure:

Male albino Wistar rats weighing 150-200 g were used for the study. The animals were maintained in polypropylene cages with husk bedding and stainless steel lids. The rats were fed with commercial rat diet and Aquaguard water ad libitum. The experiment was designed and conducted in accordance with the animal ethical norms approved by Ministry of Social Justices and Empowerment, Government of India and after approval by Institutional Animal Ethical Committee of T N Medical College and BYL Nair Hospital, Mumbai.

The hair on the dorsum of the rats was removed with the help of a sterile razor under ketamine-xylazine anaesthesia. The animals were then randomized to 6 different groups, each containing 6 animals, as shown in Table 1 below. The efficacy of the topical oil formulation NM-2 in comparison with the individual ingredients Brassica compestris oil (Mustard Oil), Bees wax, Dryobalanops camphora (Camphor) and Voveran emulgel a commercially available preparation were evaluated.

TABLE 1

| No. | Group Description | No. of Animal | Dose of study drug |
|---|---|---|---|
| 1 | Disease Control | 6 | — |
| 2 | Diclofenac | 6 | 1 g of 1% w/w gel (Voveran emulgel) |
| 3 | NM-2 Formulation | 6 | 1 ml |
| 4 | Mustard Oil | 6 | 1 ml |
| 5 | Bees Wax | 6 | 1 g |
| 6 | Camphor | 6 | 1 ml |

The study medications were applied topically on the shaven backs of the animals for 7 consecutive days. On the 8th day, the test drugs were applied as usual and 30 minutes later, carrageenan solution (0.1 ml of 1% w/v solution) was injected subcutaneously into the plantar side of the right hind paw of the animals of all the groups. The paw was marked with ink at the level of the lateral malleolus and immersed in mercury up to this mark. The paw volume was measured plethysmographically immediately before (0 hrs), and at 1 hr, 2 hrs, 3 hrs, 4 hrs, 5 hrs and 24 hrs following carrageenan injection. Values for anti-inflammatory activity were expressed as percentage change in paw volume as follows:

$$\text{Percentage change in paw volume} = ((V_t - V_o)/V_o) \times 100$$

Where $V_t$ = Paw volume 5 hours after carrrageenan injection $V_o$ = Paw volume at 0 hour Statistical Analysis:

All values are expressed as mean±SD. Statistical analysis was applied using. Graph pad PRISM 5 software (Graph pad Software Inc., San Diego, Calif.). For determination of the percentage change in paw volume, one-way analysis of variance (ANOVA), followed by Tukey's post-hoc test was carried out to identify significant differences among the groups.

TABLE 2

Effect of Diclofenac, NM-2 and individual ingredients of on carrageenan induced paw oedema in rats:

| Group | 0 hr | 2 hr | 5 hr | 24 hr |
|---|---|---|---|---|
| Disease Control | 0.25 ± 0.05 | 0.77 ± 0.06 | 0.62 ± 0.05 | 0.55 ± 0.08 |
| Diclofenac | 0.23 ± 0.05 | 0.67 ± 0.06 | 0.38 ± 0.05*** | 0.20 ± 0.05*** |
| NM-2 | 0.28 ± 0.05 | 0.71 ± 0.01 | 0.33 ± 0.05*** | 0.21 ± 0.05*** |
| Mustard Oil | 0.29 ± 0.02 | 0.71 ± 0.08 | 0.36 ± 0.09*** | 0.35 ± 0.05*** |
| Camphor | 0.33 ± 0.05 | 0.7 ± 0.05 | 0.62 ± 0.06 | 0.50 ± 0.06### |
| Bees Wax | 0.31 ± 0.04 | 0.75 ± 0.05 | 0.66 ± 0.08 | 0.59 ± 0.10### |

Values are expressed as Mean ± SD (n = 6 per group).
*$P < 0.05$,
**$P < 0.01$ and
***$P < 0.001$ when compared with the Disease control group.
$P < 0.001$ when compared with the NM-2 group.
@$P < 0.05$,
@@$P < 0.01$ and
@@@$P < 0.001$ when compared with the Diclofenac group The above Table 2 as well as FIG. 1 shows that the maximum inflammation in the paws of the animals was seen at 2 hrs after carrageenan injection. There was a significant decrease in the paw volume of rats treated with NM-2 formulation as compared with disease control ($P<0.05$), Diclofenac and individual ingredients of the NM-formulation.

TABLE 3

Effect of Diclofenac, NM-2 & Individual Ingredients on percentage change in Carrageenan induced paw oedema in rats:

| Group | Time | | |
|---|---|---|---|
| | 2 hr | 5 hr | 24 hr |
| Disease Control | 224.44 ± 79.09 | 161.11 ± 63.82 | 131.94 ± 55.88 |
| Diclofenac | 202.5 ± 79.48 | 75 ± 82.15* | −16.66 ± 25.81*** |
| NM-2 Formulation | 156.11 ± 46.25 | 19.44 ± 22.15*** | −19.44 ± 40.02*** |
| Mustard Oil | 145.77 ± 20.83 | 36.66 ± 26.24** | 20 ± 16.32*** |
| Camphor | 113.88 ± 30.12 | 90.27 ± 28.09 | 51.38 ± 18.57** |
| Bees Wax | 141.66 ± 29.34 | 112.5 ± 24.57## | 90.27 ± 38.87 |

Figure 2:
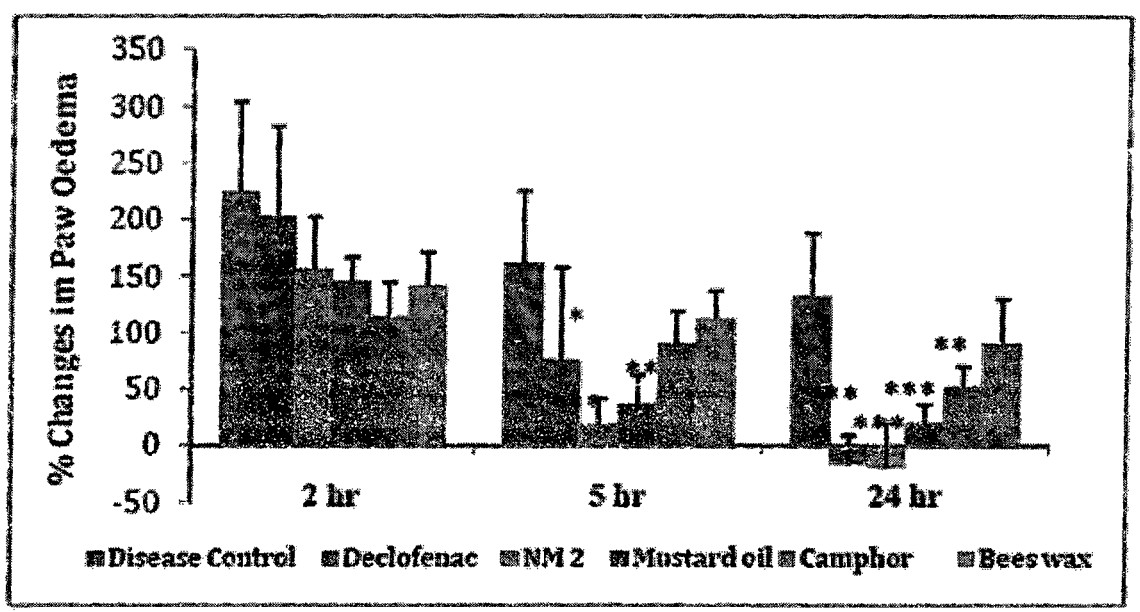
FIG. 2 illustrates effect of Dicolfenac, NM-2 (the formulation of the present invention) in comparison with its individual ingredients that is mustered oil, camphor and bees wax and commercially available preparation Dicolfenac on percent change in carrageenan induced paw odema volume.

Values are expressed as Mean ± SD (n = 6 per group).
*$P < 0.05$,
**$P < 0.01$ and
***$P < 0.001$ when compared with the Disease control group.
$P < 0.01$ when compared with the NM-2 group.
@$P < 0.05$,
@@$P < 0.01$ and
@@@$P < 0.001$ when compared with the Diclofenac group The above Table 3 as well as FIG. 2 shows that the percentage decrease in paw volume was significant in NM-2 group ($P<0.001$) when compared with Disease Control, Diclofenac group ($P<0.05$) as well as individual ingredients groups. Also, the maximal & earliest benefit was seen with the NM-2 formulation Summary:

NM-2 formulation showed a significant decrease in paw volume thereby indicating decrease in inflammation which was manifested as analgesic effect. Amongst the three ingredients of NM-2, only mustard oil showed anti-inflammatory effect that was statistically significant. However this effect as well combined effects of all the three ingredients that is Mustard Oil, Bees wax and Camphor was much lesser than that seen with the NM-2 formulation. Thus the anti-inflammatory and analgesic activity of NM-2 is due to the synergistic effects of its individual ingredients. To conclude, NM-2 formulation has shown significant promise in alleviating the inflammation and analgesia.

Example 3

Evaluation of Effect of the Topical Oil Formulation in Comparison with its Individual Ingredients in REM Sleep Deprivation Induced Hyperalgesia Chronically restricted sleep has today become a widespread and serious problem in our Society. Sleep deprivation is quite often thought of as a stressor, since various studies have shown activation of the classical stress systems and elevated plasma levels of stress hormones such as adrenaline and cortisol. Sleep per se appears to have suppressive effects on the stress systems and, consequently, sleep deprivation maintains the activity of these systems at the higher level that occurs during wakefulness. Stress can have bilateral effects on pain-related phenomena. Although acute stress can produce analgesia in animals and humans; chronic or repetitive stress has also been reported to produce hyperalgesia (increased sensitivity to painful stimuli) or allodynia (pain triggered by innocuous stimuli). The rapid eye movement (REM) sleep deprivation rat model is one model wherein it has been shown that sleep deprivation resulted in increased pain response to painful electrical stimuli, which is an indirect indicator of stress.

This experimental study was thus aimed to evaluate the potential of a NM-2 formulation and its individual ingredients to ameliorate or decrease REM sleep deprivation (insomnia) associated stress induced hyperalgesia.

Materials and Methods:

2 techniques were used in the study; the Modified flowerpot technique & hot plate method.

Rationale for Modified Flowerpot Technique:

The modified flowerpot technique was used to induce REM sleep deprivation. In this method, rats are placed on elevated platforms in a water tank for 96 hrs. During REM sleep muscle atonia occurs as a result of which when an animal enters REM sleep it falls from the platform into the water. Therefore the animal wakes up and climbs onto platform again. This method prevents REM sleep and permits other sleep stages. When such sleep deprived animals are subjected to a noxious stimulus such as hot plate, they show reduced pain threshold and increased sensitivity to pain as compared to animals who are not sleep deprived.

Rationale for Hot Plate Method:

The paws of rats are very sensitive to heat at temperatures which are not damaging to the skin. The responses shown by rats placed on a hot plate are jumping, withdrawal of the paws and licking of the paws. This test is thus used to assess the pain threshold and the animal's response to mild painful stimuli.

Study Procedures:

Male albino Wistar rats weighing 150-200 g were used for the study. The animals were maintained in polypropylene cages with husk bedding and stainless steel lids. The rats were fed with commercial rat diet and Aquaguard water ad libitum. The temperature conditions of the animal housing facility were maintained at 25±2° C. and relative humidity at 65±5%. The experiment was designed and conducted in accordance with the animal ethical norms approved by Ministry of Social Justices and Empowerment, Government of India and after approval by Institutional Animal Ethical Committee of T N Medical College and BYL Nair Hospital, Mumbai.

The hair on the dorsum of the rats was removed with the help of a sterile razor under ketamine-xylazine anaesthesia. The animals were then randomised to 6 groups each containing 6 animals as shown in Table 4 below. Diclofenac, a non-steroidal anti-inflammatory agent (NSAID) was used as the positive control for 2 reasons; firstly there is not known topical anti-stress or insomnia agent available and secondly, the parameter being assessed is response to noxious stimuli.

The study was carried out to evaluate the efficacy of the formulation NM-2 in comparison with its individual ingredients Mustard Oil, Bees Wax and Camphor and commercially available preparation Diclofenac.

TABLE 4

Grouping of animals for the study:

| No. | Group Description | No. of Animal | Dose of study drug |
|---|---|---|---|
| 1 | Disease Control | 6 | — |
| 2 | Diclofenac | 6 | 1 g of 1% w/w gel (Voveran emulgel) |
| 3 | NM-2 Formulation | 6 | 1 ml |
| 4 | Mustard Oil | 6 | 1 ml |
| 5 | Bees Wax | 6 | 1 g |
| 6 | Camphor | 6 | 1 ml |

To induce sleep deprivation, an acrylic box (24 cm×18 cm×18 cm) with platforms of height 9 cm and 6 cm diameter was used. Water was filled, in the box upto a level of 1 cm below the platform. 6 animals were placed on each platform for 96 hrs. One platform was kept vacant to reduce immobilization stress. At the end of 96 hrs, the animals were removed from the box and subjected to testing with hot plate. The temperature of the hot plate was set to 50±2° C. The responses of the animals to painful stimuli were observed (licking of paws, jumping, paw withdrawal) and the duration of time the animal could remain on the hot plate was recorded. The test substances were then applied to the back of the respective animals. One hour after application of the test substances, the animals were again subjected to the hot plate and the response was evaluated. The cut-off time was set as 60 seconds. The results are reported as paw withdrawal time before and after application of test substances and percentage change in the pain threshold which was calculated as follows:

$$\% \text{ change in pain threshold} = \frac{Rt - Ro \times 100}{Ro}$$

Where Rt=paw withdrawal time after application of test substance
Ro=paw withdrawal time before application of test substance Statistical Analysis:

All values are expressed as mean±SD. Statistical analysis was applied using Graph pad PRISM 5 software (Graph pad Software Inc., San Diego, Calif.). For determination of the percentage change in pain threshold, one-way analysis of variance (ANOVA), followed by Tukey's post-hoc test was carried out to identify significant differences among the groups. To determine paw withdrawal time, two-way ANOVA followed by Bonferroni post-hoc analysis was used with treatment and time as the two variables. A value of $P<0.05$ was considered statistically significant.

Results:

Effect of Diclofenac, NM-2 formulation and its individual ingredients of on paw withdrawal time in REM sleep deprivation induced hyperalgesia

TABLE 5

| Groups | Paw withdrawal time (Sec) | | Increase in paw withdrawal time |
|---|---|---|---|
| | Before formulation | After formulation | |
| Disease Control | 5.50 ± 1.22 | 3.83 ± 0.89 | −1.67 |
| Diclofenac | 6.67 ± 3.33 | 12.67 ± 1.96** | 6.00 |
| NM-2 | 6.83 ± 2.23 | 34.00 ± 8.67*** | 27.17 |
| Mustard Oil | 8.83 ± 2.92 | 15.83 ± 2.23### | 7.00 |
| Camphor | 4.50 ± 1.38 | 10.67 ± 2.16### | 6.17 |
| Bees Wax | 3.00 ± 1.41 | 5.67 ± 0.82### | 2.67 |

Values are expressed as mean ± SD (n = 6 per group).
* $P < 0.05$,
** $P < 0.01$ and
*** $P < 0.001$ when compared with the Disease control group,
@ $P < 0.05$,
@@ $P < 0.01$ and
@@@ $P < 0.001$ when compared with the Diclofenac group,
$P < 0.05$,
$P < 0.01$ and
$P < 0.001$ when compared with the NM 2 group.

Figure 3:
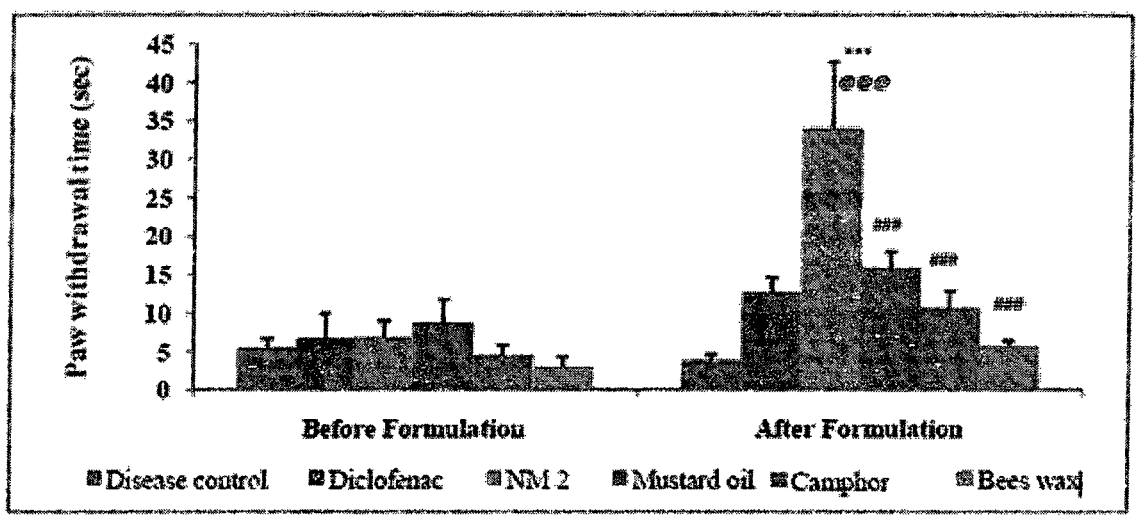
FIG. 3 illustrates effect of Dicolfenac, NM-2 (the formulation of the present invention) in comparison with its individual ingredients that is mustered oil, camphor and bees wax and commercially available preparation Dicolfenac on paw withdrawal time in REM sleep deprivation induced hyperalgesia.
Figure 4:
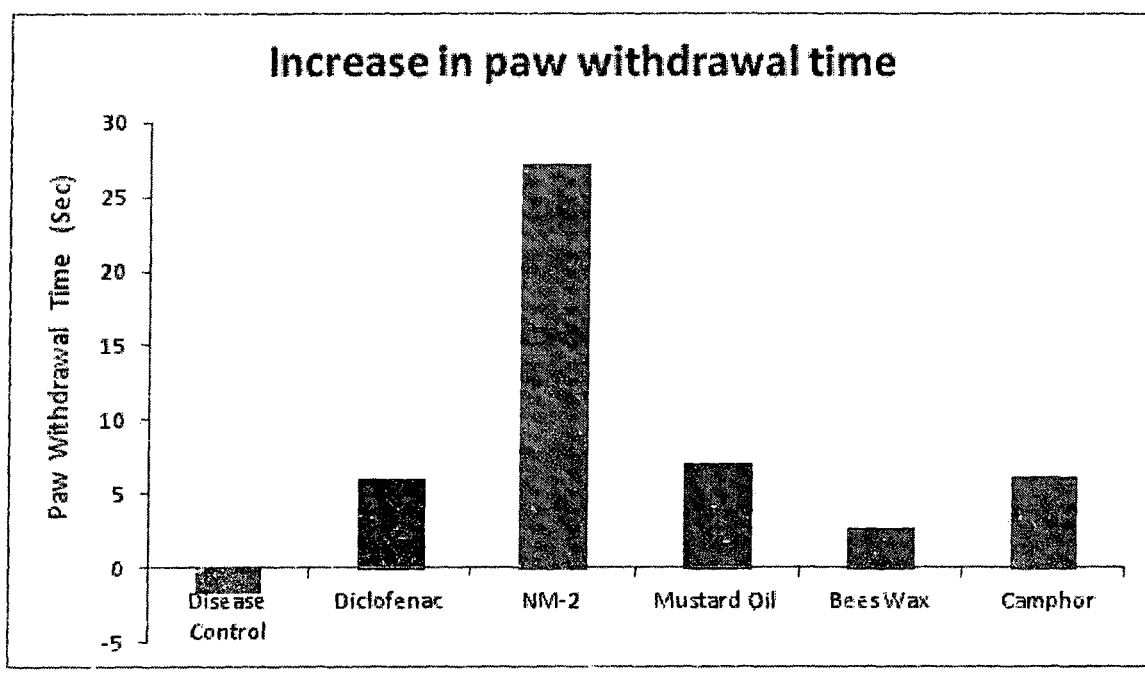
FIG. 4 illustrates effect of Dicolfenac, NM-2 (the formulation of the present invention) in comparison with its individual ingredients that is mustered oil, camphor and bees wax and commercially available preparation Dicolfenac on increase in paw withdrawal time in REM sleep deprivation induced hyperalgesia.

The above Table 5 as well as FIGS. 3 and 4 show that: there was a significant increase in the pain threshold in rats of NM-2 groups ($P<0.001$) as compared with control group, Diclofenac ($P<0.05$) and individual ingredients groups (refer Table 5 & FIG. 3); further the percentage increase in pain threshold of NM-2 group manifested in terms of Increase in paw withdrawal time was significantly highest of NM-2 group as compared to the Diclofenac group as well as individual ingredients groups (refer Table 5 & FIG. 4)

Summary

Treatment with NM-2 formulation showed significant increase in paw withdrawal time and thus significant increase in percentage of pain threshold when compared with disease control group. The effect seen with NM-2 formulation was greater than each of its individual ingredients, indicating that the activity of NM-2 in overcoming REM sleep deprivation induced hyperalgesia is due to the synergistic effects of its individual ingredients. Thus the efficacy of NM-2 formulation in alleviating sleep deprivation induced hyperalgesia, indicates that it may have stress relieving properties.

In view of the above results it is seen that the various effects of formulation of the present invention attained are due to synergistic activities of its individual ingredients.

Having described the disclosure in detail, it will be apparent that modifications and variations are possible in the above compositions, products, and methods without departing from the scope of the disclosure defined in the appended claims.

The invention claimed is:

1. A composition that relieves one or more of the conditions of pain, stress and insomnia, wherein said composition comprises *Brassica campestris* oil in the range of 40 to 75 weight parts of the composition, bees wax in the range of 15 to 50 weight parts of the composition and *Dryobalanops camphora* in the range of 1 to 20 weight parts of the composition, wherein the *Brassica campestris* oil, bees wax and *Dryobalanops camphora* are present in a ratio of about 1:0.5:0.1.

2. The composition as claimed in claim 1, wherein the *Brassica campestris* oil is in the range of 55 to 65 weight parts of the composition, bees wax is in the range of 25 to 35 weight parts of the composition and *Dryobalanops camphora* is in the range of 3 to 13 weight parts of the composition, wherein the *Brassica campestris* oil, bees wax and *Dryobalanops camphora* are present in a ratio of about 1:0.5:0.1.

3. The composition as claimed in claim 1, wherein the composition further comprises one or more of oil and perfume.

4. The composition as claimed in claim 1, wherein the composition further comprises one or more natural or synthetic active ingredients, pharmaceutically acceptable excipients or combinations thereof.

5. A formulation comprising the composition as claimed in claim 1.

6. A formulation comprising the composition as claimed in claim 2.

7. A method for preparing a formulation comprising the composition as claimed in claim 1, wherein the method comprises: heating 40 to 75 weight parts of *Brassica campestris* oil at a temperature of 60° C.-225° C.; mixing 15 to 50 weight parts of bees wax in the hot *Brassica campestris* oil until the bees wax is dissolved; taking the mixture away from the source of heat; adding to the mixture 1 to 20 weight parts of *Dryobalanops camphora* and mixing, and wherein the *Brassica campestris* oil, bees wax and *Dryobalanops camphora* are present in a ratio of about 1:0.5:0.1.

8. The method of claim 7, wherein the time period for heating of *Brassica campestris* oil is a time period sufficient to attain the temperature of 60° C.-100° C.

9. The method of claim 7, wherein the *Brassica campestris* oil is 55 to 65 weight parts of the composition.

10. The method of claim 7, wherein the Bees wax is 25 to 35 weight parts of the formulation.

11. The method of claim 7, wherein the *Dryobalanops camphora* is 3 to 13 weight parts of the formulation.

12. The method of claim 7, wherein the method further comprises adding one or more of other natural or synthetic active ingredients and or pharmaceutically acceptable excipients.

13. A method of treating one or more of the conditions of pain, stress and insomnia, comprising applying the formulation sufficient to cover affected areas, inflamed areas, head or all over body in a subject in need thereof, as according to claim 5.

14. A method of treating one or more of the conditions of pain, stress and insomnia, comprising applying the formulation sufficient to cover affected areas, inflamed areas, head or all over body in a subject in need thereof, as according to claim 6.

15. The composition as claimed in claim 1, wherein the *Dryobalanops camphora* is in a crystal or an oil form.

16. A composition that relieves one or more of the conditions of pain, stress and insomnia, wherein said composition consists essentially of *Brassica campestris* oil in the range of 40 to 75 weight parts of the composition, bees wax in the range of 15 to 50 weight parts of the composition and *Dryobalanops camphora* in the range of 1 to 20 weight parts of the composition, wherein the *Brassica campestris* oil, bees wax and *Dryobalanops camphora* are present in a ratio of about 1:0.5:0.1.

17. A composition that relieves one or more of the conditions of pain, stress and insomnia, wherein said composition consists of *Brassica campestris* oil in the range of 40 to 75 weight parts of the composition, bees wax in the range of 15 to 50 weight parts of the composition and *Dryobalanops camphora* in the range of 1 to 20 weight parts of the composition, wherein the *Brassica campestris* oil, bees wax and *Dryobalanops camphora* are present in a ratio of about 1:0.5:0.1, and optionally, a pharmaceutically acceptable carrier.

18. The composition as claimed in claim 1, wherein the composition has only three active ingredients: *Brassica campestris* oil, bees wax, and *Dryobalanops camphora*.

\* \* \* \* \*